United States Patent [19]

Kenney

[11] Patent Number: 4,589,987

[45] Date of Patent: May 20, 1986

[54] SEPARATING ANIMAL CELLS FROM A LIQUID CULTURE

[75] Inventor: Andrew C. Kenney, Windsor, England

[73] Assignee: Celltech Limited, Slough, Berkshire, United Kingdom

[21] Appl. No.: 728,294

[22] Filed: Apr. 29, 1985

[30] Foreign Application Priority Data

May 2, 1984 [GB] United Kingdom ................. 8411192

[51] Int. Cl.$^4$ ............................ C02F 1/54; C12N 1/02
[52] U.S. Cl. .................................... 210/725; 210/730; 210/927; 435/241; 435/261; 435/803
[58] Field of Search ............... 210/725, 730, 729, 927, 210/738, 905; 435/261, 241, 803; 426/1

[56] References Cited

U.S. PATENT DOCUMENTS

| | | | |
|---|---|---|---|
| 3,982,003 | 9/1976 | Mitchell et al. | 426/1 |
| 4,105,804 | 8/1978 | Tervi et al. | 435/261 |
| 4,399,223 | 8/1983 | Vanderveen et al. | 435/261 |
| 4,440,867 | 4/1984 | Sabherwal | 210/660 |

FOREIGN PATENT DOCUMENTS

| | | | |
|---|---|---|---|
| 149870 | 8/1981 | Fed. Rep. of Germany | 435/261 |
| 52-31884 | 3/1977 | Japan | 435/261 |

*Primary Examiner*—Benoît Castel
*Attorney, Agent, or Firm*—Cushman, Darby & Cushman

[57] ABSTRACT

A process for separating animal cells and/or animal cell debris from a liquid culture of animal cells involves flocculating the culture with a polygalacturonic acid and separating the flocculated animal cells and/or animal cell debris from the liquid culture.

6 Claims, No Drawings

SEPARATING ANIMAL CELLS FROM A LIQUID CULTURE

This invention relates to a process for separating animal cells and/or animal cell debris from a liquid culture of animal cells. The process is well suited for the separation of hybridoma cells from liquid culture.

The recent advances in molecular biology have led to an increased demand for refined fermentation processes and apparatus. In particular, animal cells, modified by various techniques, are widely being cultured for the extraction of polypeptides and proteins produced by them. A step in the process is the separation of animal cells and/or animal cell debris from the culture liquid. This is a necessary first stage in the isolation of cell products from the culture liquid.

Conventionally the separation is achieved by centrifugation of the liquid culture of animal cells. This is generally inefficient, considerable acceleration being necessary for a relatively long period to ensure complete separation. Alternatively, the liquid culture may be filtered but the filters become easily blocked with animal cells and debris. In both techniques useful cell products may be removed and discarded with the animal cells and there may be an incomplete separation of cellular debris from the culture supernatant.

The object of the present invention is to increase the efficiency of the separation of animal cells from a liquid culture medium.

It is known to flocculate microbial liquid cultures to assist in the separation of microbial cells from the culture. An example of such a process is the addition of finings to cloudy ale. The finings causes small particles of yeast and yeast debris to flocculate and subsequently to settle to the bottom of the brewing vessel.

Animal cellular material, under ordinary conditions has a net negatively charged outer surface. Since flocculation occurs by the linking of particles of opposite polarity due to electrostatic attractive forces, it might be expected that positively charged material would flocculate animal cells and animal cell debris. We have surprisingly discovered however that a negatively charged soluble polymer has great efficacy in causing the flocculation of animal cells and animal cell debris. Furthermore, of the negatively charged soluble polymers that we tested only one shows an appreciable flocculating effect. We hypothesise that this may be due to the charge distribution on the polymer matching positive local regions of charge on the cells.

According to the present invention we provide a process for separating animal cells and/or animal cell debris from a liquid culture of animal cells comprising the steps of flocculating the animal cells and/or animal cell debris by mixing a polygalacturonic acid with the culture and separating the flocculated animal cells and/or animal cell debris from the liquid culture.

The use of a polygalacturonic acid as a flocculating agent in this way has legion advantages. The flocculation of the animal cells and/or animal cell debris prior to physical separation increases dramatically the potential product yield and purity of a culture and speeds up the separation process as a whole. Not only is the process of the invention effective in flocculating animal cells but it is also effective in flocculating animal cell debris which as a result of small size often proves problematical to remove. Furthermore, very little of the animal cell product is removed from the culture supernatant by the process of the invention. Polygalacturonic acid itself is non-toxic, readily available and cheap. It is obtained by deacylating pectin.

The polygalacturonic acid may be polygalacturonic acid itself or any soluble derivative of polygalacturonic acid capable of causing flocculation of animal cells or of animal cell debris. The molecular weight of the polygalacturonic acid may be varied widely provided that the polymer used is substantially soluble under the conditions found in a liquid culture of animal cells. Similarly the concentration of the polygalacturonic acid used may be varied widely and indeed because of the dependence of the effective concentration upon cell density cannot be accurately defined. However, the upper viable limit is set by a concentration at which the polygalacturonic acid causes the culture to set into a gel. This clearly is undesirable. The lower limit is set by the concentration at which a substantial flocculation of the animal cells or cell debris occurs. For a typical culture we prefer to use a concentration of polygalacturonic acid of at least 0.004% (weight/volume). Most preferably a concentration of about 0.03% (weight/volume) is used.

The flocculated animal cells and/or animal cell debris may be separated from the liquid by filtration or centrifugation optionally after allowing the flocculated animal cells and/or animal cell debris to settle under the influence of gravity. The resulting supernatant is clear and may readily be purified to obtain the polypeptide or protein produced by the animal cells. The process may, of course, be applied to a liquid culture of animal cells following disruption of the cells, for example, by sonication.

The animal cells may be naturally occurring animal cells capable of in vitro growth but are preferably genetically-modified animal cells. Preferably the animal cells are hybridoma cells, for example, mouse or rat-derived hybrid cells. Alternatively the animal cells may be human lymphoblastoid cells. In the case where the animal cells produce antibody (IgM or IgG) very little antibody is removed from the liquid part of the culture during flocculation of the animal cells and/or animal cell debris, thereby maintaining a high yield of antibody.

Preferably the liquid culture is adjusted to an acid pH at least during flocculation. The acid pH tends to ensure protonation of amino groups and histidine residues on the cell surface and hence increases the charge of positive regions on the cell. The polymer remains ionised at a pH less than pH 3. Preferably the pH is adjusted to between pH 4 and pH 7, most preferably between pH 5 and pH 6.

The liquid culture may be any suitable medium, for example, Dulbecco Modfied Eagle Medium (DMEM) or L-Broth.

The invention is now described by way of example only, with reference to the following Examples.

EXAMPLE 1

An experiment was conducted to demonstrate the flocculating capabilities of a number of negatively charged soluble polymers on a culture of hybridoma cells producing IgM in culture. The results of this experiment emphasise the singular properties of polygalacturonic acid in this respect.

Hybridoma cells (NB1- a mouse hybridoma) producing IgM were grown using standard roller culture techniques in a medium comprising Dulbecco Modified Eagle Medium (DMEM) and 5% foetal calf serum. The culture was used at the end of the logarithmic phase of growth when the cell density and the quantity of cell debris was at a maximum. Aqueous solutions of the following negatively charged polymers were prepared; polygalacturonic acid (4% w/v); dextran sulphate M.W. 8000 (10% w/v); dextran sulphate M.W. 500,000 (8% w/v); alginic acid; carageenan, DEAE-dextran; polyglutamic acid and polyvinylsulphate.

Volumes of the culture (50 ml) were adjusted to pH 5.0, 7.0 and 9.0 respectively using either 1M HCl or solid Tris-HCl base. The flocculating agent under test was added to 10 ml of each pH adjusted sample in a 15 ml graduated tube and each sample was mixed by inversion. Each tube was allowed to stand and was observed after 2 hours and 18 hours. One series of tubes containing polygalacturonic acid at pH 5.0 was clarified by centrifugation. The cleared supernatants were sampled and the IgM concentration was measured using an ELISA assay.

The results of the experiment are given in Table 1.

TABLE 1

| Flocculating Agent | Concentration % w/v | pH 5.0 | pH 7.0 | pH 9.0 |
|---|---|---|---|---|
| polygalacturonic acid | 0.04 | Extensive flocuulation after 2 hrs. at each pH. At pH 5.0 the supernatant clarity was judged better than at pH 7.0 or pH 9.0 | | |
|  | 0.004 | as above | | |
|  | 0.0004 | no flocculation | | |
| dextran sulphate M.W. 8000 | 1.0 | no flocculation | | |
| dextran sulphate M.W. 500,000 | 0.3 | no flocculation | | |
| no flocculating agent (control) |  | no flocculation | | |

Alginic acid, carageenan, D.E.A.E.-dextran, polyglutamic acid and polyvinylsulphate failed to induce flocculation at a concentration of 1% (w/v). No loss of IgM could be detected in supernatants arising from culture flocculated with between 0.04% (w/v) and 0.0004% (w/v) polygalacturonic acid.

EXAMPLE 2

The experiment described in Example 1 demonstrated the efficacy with which polygalacturonic acid flocculates hybridoma cells in liquid culture. This part of the experiment was scaled up to a pilot plant level.

A 30 liter culture was grown and harvested in the following way. The pH of the culture was reduced to between 5.0 and 6.0 by blowing $CO_2$ into the culture fermenter. Polygalacturonic acid was added at a concentration of between 0.04 and 0.1% (w/v) depending upon the hydridoma cell and cell debris density. The volume of the flocculating agent added was about 50 ml. After mixing in the fermenter, the gas supply was stopped and the flocculation was allowed to proceed, the flocculated cells and debris being allowed to settle for 1 hour. Subsequently the flocculated cells and debris were removed either by filtration using a wound polypropylene depth filter cartridge (nominal $0.1\mu$ pore size) or by continuous centrifugation using a Westfalia SA-1 separator. In both cases the resultant supernatant was judged to be clearer than that which may be obtained using conventional separation techniques. This scaled up experiment was repeated successfully with 100 and 1000 liter cultures. It was shown that, in addition, the pH could be reduced using 5M $H_2SO_4$ and that the polygalacturonic acid can be dissolved in water to a concentration of 20% (weight/volume) prior to addition for ease of handling.

EXAMPLE 3

The experiment described in Example 2 was repeated in a 100 liter culture using a mouse hybridoma cell-line and a human lymphoblastoid cell-line (EB transformed lymphocytes). In both cases successful flocculation and separation of the animal cells and animal cell debris was achieved.

It will of course be understood that the present invention has been described above purely by way of example, and modifications of detail can be made within the scope and spirit of the invention.

I claim:

1. A process for separating animal cells or animal cell debris from a liquid culture of animal cells comprising the steps of flocculating the animal cells or animal cell debris by mixing an effective amount of polygalacturonic acid with the culture to cause flocculation of the animal cells or animal cell debris and separating the flocculated animal cells or animal cell debris from the liquid culture.

2. A process according to claim 1 wherein the flocculated animal cells or animal cell debris are separated from the liquid culture by filtration or centrifugation.

3. A process to claim 1 wherein the animal cells are genetically-modified animal cells.

4. A process according to claim 3 wherein the animal cells are hybridoma cells.

5. A process according to claim 3 wherein the animal cells are lymphoblastoid cells.

6. A process according to claim 1 wherein the pH of the liquid culture is adjusted to an acid pH at least during flocculation.

* * * * *